(12) United States Patent
Manissier et al.

(10) Patent No.: US 9,000,049 B2
(45) Date of Patent: Apr. 7, 2015

(54) COMBINATION OF LYCOPENE, POLYPHENOL, AND VITAMINS FOR THE CARE OF KERATIN MATERIALS

(75) Inventors: Patricia Manissier, Levallois-perret (FR); Christiane Montastier, Paris (FR); Antoine Piccirilli, Poitiers (FR)

(73) Assignee: Laboratories Inneov SNC, Asnieres (FR)

( * ) Notice: Subject to any disclaimer, the term of this patent is extended or adjusted under 35 U.S.C. 154(b) by 212 days.

(21) Appl. No.: 13/132,539

(22) PCT Filed: Dec. 3, 2009

(86) PCT No.: PCT/IB2009/055489
§ 371 (c)(1),
(2), (4) Date: Aug. 1, 2011

(87) PCT Pub. No.: WO2010/064210
PCT Pub. Date: Jun. 10, 2010

(65) Prior Publication Data
US 2011/0281941 A1 Nov. 17, 2011

Related U.S. Application Data

(60) Provisional application No. 61/122,985, filed on Dec. 16, 2008.

(30) Foreign Application Priority Data

Dec. 3, 2008 (FR) ..................... 08 58235

(51) Int. Cl.
| | | |
|---|---|---|
| A61K 31/05 | (2006.01) | |
| A61K 31/355 | (2006.01) | |
| A61K 8/31 | (2006.01) | |
| A61K 8/34 | (2006.01) | |
| A61K 8/67 | (2006.01) | |
| A61K 8/97 | (2006.01) | |
| A61K 31/01 | (2006.01) | |
| A61K 31/375 | (2006.01) | |
| A61K 36/15 | (2006.01) | |
| A61Q 3/00 | (2006.01) | |
| A61Q 19/06 | (2006.01) | |
| A61Q 19/08 | (2006.01) | |

(52) U.S. Cl.
CPC ............ *A61K 31/355* (2013.01); *A61K 8/31* (2013.01); *A61K 8/347* (2013.01); *A61K 8/676* (2013.01); *A61K 8/678* (2013.01); *A61K 8/97* (2013.01); *A61K 31/01* (2013.01); *A61K 31/375* (2013.01); *A61K 36/15* (2013.01); *A61Q 3/00* (2013.01); *A61Q 19/06* (2013.01); *A61Q 19/08* (2013.01); *A61K 2800/92* (2013.01)

(58) Field of Classification Search
CPC ..................................... A61K 31/05
USPC ........................................ 514/731
See application file for complete search history.

(56) References Cited

U.S. PATENT DOCUMENTS

| | | | |
|---|---|---|---|
| 5,844,061 A | | 12/1998 | Vercauteren et al. |
| 6,348,200 B1 * | | 2/2002 | Nakajima et al. ............ 424/401 |
| 6,605,296 B1 | | 8/2003 | Stuckler |
| 6,623,769 B1 | | 9/2003 | Lorant et al. |

FOREIGN PATENT DOCUMENTS

| | | |
|---|---|---|
| EP | 1 090 628 A1 | 4/2001 |
| FR | 2 706 478 A1 | 12/1994 |
| JP | A-8-283136 | 10/1996 |
| JP | B2-2940964 | 6/1999 |
| JP | A-2003-146899 | 5/2003 |
| KR | A-10-2006-0022369 | 3/2006 |
| WO | WO 97/47278 A1 | 12/1997 |
| WO | WO 01/91588 A1 | 12/2001 |
| WO | WO 02/34210 A2 | 5/2002 |
| WO | WO 2006/000226 A1 | 1/2006 |
| WO | WO 2007/112996 A2 | 10/2007 |

OTHER PUBLICATIONS

American Botanical Council. Scientific and Clinical Monogrpah for Pycnogenol. 2008.*
Richelle M1, Bortlik K, Liardet S, Hager C, Lambelet P, Baur M, Applegate LA, Offord EA. A food-based formulation provides lycopene with the same bioavailability to humans as that from tomato paste. J Nutr. Mar. 2002;132(3):404-8.*
Segger et al., "Supplementation with Evelle® improves skin smoothness and elasticity in a doubleblind, placebo-controlled study with 62 women," *Journal of Dermatological Treatment*, 2004, pp. 222-226, vol. 15.
Choi et al., "Cosmeceuticals," *Seminars in Cutaneous Medicine and Surgery*, 2006, pp. 163-168, Elsevier Inc.
Liu et al., "The scavenging capacity and synergistic efforts of lycopene, vitamin E, vitamin C, and β-carotene mixtures on the DPPH free radical," *LWT*, 2008, pp. 1344-1349, vol. 41, Elsevier Ltd.
Fuchs et al., "Modulation of UV-Light-Induced Skin Inflammation By $_D$-Alpha-Tocopherol and $_L$-Ascorbic Acid: A Clinicalstudy Using Solar Simulated Radiation,"*Free Radical Biology & Medicine*, 1998, pp. 1006-1012, vol. 25, No. 9, Elsevier Science Inc.
Rohdewald, "A review of the French maritime pine bark extract (Pycnogenol®), a herbal medicationwith a diverse clinical pharmacology," International Journal of Clinical Pharmacology and Therapeutics, vol. 40, No. 4, Apr. 2002, pp. 158168.
International Search Report for International Patent Application No. PCT/IB2009/05489, mailed on Feb. 3, 2010 (w/ English translation).

* cited by examiner

*Primary Examiner* — Paul Zarek
(74) *Attorney, Agent, or Firm* — Oliff PLC

(57) ABSTRACT

The present invention relates to the cosmetic use, by the oral route, of a combination of lycopene, of vitamin C, of vitamin E and of at least one polyphenol compound derived from pine bark as active ingredient intended for maintaining and/or restoring the biomechanical properties of keratinous materials, and notably of the skin.

18 Claims, No Drawings

COMBINATION OF LYCOPENE, POLYPHENOL, AND VITAMINS FOR THE CARE OF KERATIN MATERIALS

The present invention relates to the area of dietary supplements intended for care of the skin. Thus, it relates to the use of a composition for oral and/or parenteral administration comprising a combination of active ingredients intended for maintaining and/or restoring the biomechanical properties of keratinous materials such as connective tissues, and more particularly of the skin. It also relates to a composition for administration by the oral and/or parenteral route constituted of a particular combination of said active ingredients.

Human skin is constituted of three compartments: the epidermis, the dermis and the hypodermis. The last-mentioned compartment is essentially constituted of a type of cells specialized in the accumulation and storage of fats, the adipocytes. The hypodermis is the body's energy reservoir.

The natural human epidermis is mainly composed of three types of cells: keratinocytes, constituting the majority, melanocytes and Langerhans' cells. Each of these cellular types contributes, by its particular functions, to the essential role performed by the skin.

The dermis supplies the skin with a solid support. It is also its nutrient element. It is mainly constituted of fibroblasts and of an extracellular matrix composed in its turn principally of collagen, elastin and a substance, called ground substance, these components being synthesized by the fibroblasts.

There are also leukocytes, mastocytes or else tissue macrophages. It is also traversed by blood vessels and nerve fibers. In normal skin, i.e. neither pathological nor scarred, the fibroblasts are in a quiescent state, i.e. nonproliferative.

It is the collagen fibers that provide the solidity of the dermis. The collagen fibers are constituted of fibrils that are sealed together, thus forming more than ten types of different structures. The solidity of the dermis is largely due to the interlocking of the collagen fibers packed against one other in all directions. The collagen fibers contribute to the elasticity and tonicity of the skin and/or of the mucosae.

The collagen fibers are continually renewed but this renewal decreases with age, leading to thinning of the dermis. This thinning of the dermis may also be due to pathological causes, for example hypersecretion of corticoid hormones, certain pathologies or also vitamin deficiencies (vitamin C in the case of scurvy). It is also assumed that extrinsic factors such as ultraviolet radiation, tobacco or certain treatments (glucocorticoids, vitamin D and derivatives for example) also have an effect on the skin and on its collagen level.

Various factors lead to degradation of collagen, with all the consequences that can be imagined on the structure and/or firmness of the skin and/or of the mucosae.

Although very strong, collagen fibers are sensitive to certain enzymes called collagenases. Degradation of collagen fibers leads to the appearance of the skin that is slack and wrinkled, which human beings, preferring the appearance of skin that is smooth and taut, have always tried to combat.

The collagenases form part of a family of enzymes called metalloproteinases (MMPs) which are themselves members of a family of proteolytic enzymes (endoproteases or endopeptidases) which possess a zinc atom coordinated to 3 cysteine residues and a methionine in their active site and which degrade the macromolecular components of the extracellular matrix and of the basal membranes at neutral pH (collagen, elastin, etc). Very widely distributed in living organisms, these enzymes are present, but expressed at a low level, in normal physiological situations such as growth of organs and renewal of tissues.

Their overexpression in humans and their activation is linked to many processes, sometimes pathological, which involve destruction and remodelling of the matrix. This leads either to uncontrolled resorption of the extracellular matrix, or conversely to development of a state of fibrosis.

The metalloproteinase family is constituted of several well-defined groups based on their similarities in terms of structure and substrate specificity. Among these groups, we may mention collagenases intended for degrading the fibrillar collagens (MMP-1 or interstitial collagenase, MMP-8 or neutrophil collagenase, MMP-13 or collagenase 3), gelatinases which degrade type IV collagen or any form of denatured collagen (MMP-2 or gelatinase A (72 kDa), MMP-9 or gelatinase B (92 kDa)), the stromelysins (MMP-3) whose broad spectrum of activity is applied to proteins of the extracellular matrix such as the glycoproteins (fibronectin, laminin), the proteoglycans, etc., or the membrane metalloproteinases.

Moreover, certain proteoglycans such as those belonging to the family of Small Leucine-Rich Proteoglycans (SLRPs) constitute an interesting target with a view to preventing the negative effects of aging and deterioration of the mechanical properties of the skin. These SLRPs are in fact directly involved in fibrillogenesis and hydration of the perifibrillar spaces. The SLRPs notably help to increase the bioavailability of certain growth factors such as TGF-β: among the SLRPs, we may mention decorin, lumican, fibromodulin, biglycan. Moreover, certain immunohistochemical observations show a decrease of biglycan accumulation in aging skin. Moreover, the marked decrease in lumican and fibromodulin induces a deterioration of fibrillogenesis of collagen as well as disturbance of the fibrillar architecture. Consequently, the proteoglycans of the SLRP family play a fundamental role in the architectural organization of the structures of the skin.

Finally, SLRPs are not only sensitive to the action of MMPs, but also to the proteolytic action of aggrecanases or ADAMTS (A Disentegrin and Metalloproteinase with Thrombospondin type I repeat). Certain members of this new family of metalloproteinases, in particular ADAMTS 1 and 4, have been identified in the skin, and ADAMTS4 is known to cleave decorin.

Prolonged exposure to ultraviolet radiation, especially to type A and/or B ultraviolet radiation, has the effect of stimulating the expression of collagenases, particularly of MMP-1. This is one of the components of photo-induced skin aging.

Moreover, at the menopause, the main changes affecting the dermis are a decrease of the proportion of collagen and of dermal thickness. In a post-menopausal woman this leads to thinning of the skin and/or mucosae. The woman then experiences a sensation of "papyraceous skin" or of skin that pulls, and there is accentuation of fine wrinkles and surface lines. The skin feels rough on palpation. Finally the skin displays reduced pliability.

Finally, in subjects who are overweight and more particularly during weight gain, the adipocytes tend to increase rapidly in volume (storage of increasing amounts of lipids). The fat lobules are then gradually distended, leading to the formation of strands of connective tissue, parallel to one another and perpendicular to the surface of the skin. The strong pressure exerted by the adipocytes on the dermis quickly causes deformation of the surface of the skin. Referring to the skin, this phenomenon called cellulite is reflected in a dimpled appearance giving an "orange peel" effect in places. Finally, in clinical terms, cellulite is reflected in a change of texture of the sub-cutaneous and surface tissues, characterized in particular by:

skin that is thicker overall,
skin that is more substantial, skin that is more sensitive and, depending on how advanced the cellulite is, can be painful on palpation, and/or skin tissues that are less mobile owing to loss of adherence and cohesion of the deep layers of the skin.

Furthermore, this phenomenon is more visible in women as they have a finer skin with a connective tissue framework having a vertical structure, which in men, in contrast, has an oblique, criss-cross structure.

Cellulite, which is often made worse by excess weight and obesity, is especially localized at the pelvis and the lower limbs (cellulite as "jodhpurs" or "clown's trousers"). These changes can also lead to permanent scarring deformations.

Hypertrophy of adipose tissue is accompanied at the dermal level by the networks of fibers being put under tension, leading to a functional change of the resident cells. In fact, this increased tension hampers cellular exchanges, and the venous and lymphatic circulation by compression of the capillaries, so that the phenomenon is self-maintaining. In the end, the fibers degenerate and the skin loses its fundamental structures.

Biologically, when the fibroblasts are subject to normal tissue tension, they actively synthesize collagen, elastin, and glycosaminoglycans, fundamental molecules that contribute to reinforcement of the supporting tissues of the skin. Similarly, adipocytes that are overloaded with lipids also exert a tension on the dermis, leading to overproduction of collagen as far as fibrosis.

Conversely, during weight loss and notably during slimming diets, rapid destocking of adipocytes leads to a considerable decrease in the tension exerted by the hypodermis on the supporting tissues. Consequently, as the dermis is no longer under tension, the connective tissue gradually loses its cohesion: loss of attachment of fibroblasts to collagen, decrease in amount of neocollagen, distension of elastin fibers, depolymerization of proteoglycans, etc. Accordingly, as the fibroblasts are interacting less with the fibers of the extracellular matrix, they no longer receive, from their environment, the signals for activity and repair which control the synthesis of the fundamental macromolecules of the dermis. Moreover, as the fibroblasts no longer receive signals from their fibrillar environment, they secrete matrix metalloproteinases (MMPs), enzymes causing the degradation of fibrous structures. This pronounced slowing of metabolism of the fibroblasts, and the degradation of fibers by MMPs, are reflected in consequence by a deterioration of the viscoelastic or biomechanical properties of the skin (loss of firmness, of tonicity, of elasticity, etc.).

From reading the foregoing, we can understand the importance of collagen and of glycosaminoglycans in the structure of the tissues, particularly of the skin and/or mucosae, and the importance of combating its degradation so as to counter any deterioration of the viscoelastic or biomechanical properties of the skin (loss of firmness, of tonicity, etc.), whether or not it is associated with chronobiological or photo-induced skin aging.

The invention in fact aims to propose a novel combination of active ingredients useful for alleviating and/or preventing a deterioration of the biomechanical properties of the skin and therefore the manifestation of skin disorders directly linked to said deterioration, for example, the associated disorders, thinning of the dermis and/or degradation of collagen fibers, this last-mentioned effect leading to the appearance of skin that is flabby and/or wrinkled, combating which is in fact the aim of the present invention.

The present invention relates more particularly to the prevention and/or treatment, by the oral and/or parenteral route, of skin conditions associated with a deterioration of the viscoelastic or biomechanical properties of the skin. It aims more particularly to maintain and/or restore the biomechanical properties of the skin.

More precisely, the inventors discovered that the administration, by the oral and/or parenteral route, of a combination of lycopene, vitamin C, vitamin E and at least one polyphenol compound, in particular a polyphenol compound derived from pine bark, displays a beneficial activity on keratinous materials and in particular on the constituents of the dermis, and makes it possible to combat a deterioration of the biomechanical properties of a keratinous material and/or has a favorable action notably on maintaining and/or restoring the biomechanical properties of a keratinous material, in particular of a connective tissue and more particularly of the skin.

Lycopene is a natural pigment that is present in ripe fruit, particularly in tomatoes. It belongs to the carotenoid family and its structure is similar to that of β-carotene.

The role of lycopene in the ripening of fruit is known from the prior art. Lycopene is used in compositions with tanning activity for its effect on melanin synthesis (WO 97/47278), in compositions intended for treatment of the hair and/or of acne for its activity on the 5α-reductases (JP-2940964), as an antiradical agent (JP-A-8-283136) or it is also used in compositions intended for treating, i.e. preventing and/or curing, the cutaneous signs of aging (EP 1 090 628).

The polyphenol compounds are notably known for their strong antioxidant power and are commonly used in cosmetics. Their role in preventing cardiovascular diseases by the oral route has also been described. Some of them are also used in compositions for topical application, for example in esterified form in document FR 2 706 478 so as to make them fat-soluble in order to improve their resistance to oxidation.

Vitamin C (or ascorbic acid) is known to stimulate the synthesis of collagen, by preventing, as co-factor, the autoinactivation of the enzymes lysine- and proline-hydroxylases and by increasing the synthesis of the mRNAs of procollagens. Ascorbic acid (or vitamin C) is also known for stimulating the synthesis of elastin of the skin or for treating wrinkles.

The aforementioned compounds have already been proposed in combination with other active ingredients in oral compositions, such as dietary supplements for example, notably intended to provide the subjects thus treated with a good physiological condition reflected notably in better protection against heart diseases, rheumatism, circulatory diseases (U.S. Pat. No. 6,605,296) or better appearance of the skin in terms of smoothness and softness.

The use of a combination of at least one carotenoid and vitamin C for treating the cutaneous signs of aging is known from document WO 02/34210.

Moreover, a composition for oral administration is known from document WO 2006/000226, useful for treating the cutaneous signs of aging, comprising vitamin E, vitamin C, and an extract of baitcha tea, as well as optionally an antioxidant extracted from grapeseed, tomato, soya and/or chamomile, an extract comprising glycosaminoglycans and at least one transition metal.

Finally, Segger et al. describe an oral composition that comprises, as active ingredients, a mixture of vitamins, carotenoids, selenium, zinc, amino acids, glycosaminoglycans, a bilberry extract and Pycnogenol®, which is proposed notably for treating roughness and/or a loss of elasticity of the skin (*Journal of Dermatological Treatment* (2004), 15, 222-226).

In general, loss of skin elasticity results from changes in the network of elastic fibers of the dermis but also from decrease of glycosaminoglycans, which control the fluidity of the interstitial fluid that surrounds the fibers of the dermal network. Accordingly, it is not specific to a group of the population and so can appear even at a very young age.

For its part, the present invention relates more particularly to protection, or even improvement of tonicity, firmness, pliability and/or density of the skin.

Deficiencies of tonicity, firmness, pliability and/or density of the skin most often result from skin aging but also from a state of fatigue. Thus, these deficiencies may be the direct cause of the appearance of signs of skin aging such as wrinkles and/or lines which are typically manifested from age 30 years for wrinkles, but also cutaneous signs not directly linked to age but nevertheless more particularly encountered in adults such as bags and rings under the eyes.

In terms of biological mechanism, wrinkles result from muscle loss or repeated muscular strain, loss of fat deposits, persistent gravitational forces and loss of bone and cartilage of the face. Flattening of the junction between dermis and epidermis as well as decrease of collagen IV are considered to be factors influencing the formation of wrinkles.

From a histological standpoint, the epidermis appears atrophied, a clear manifestation of ptosis of cutaneous tissues observed during loss of skin elasticity.

Unexpectedly, the inventors found that it was possible to treat the manifestation of these cutaneous signs, i.e. notably wrinkles, lines, bags and rings under the eyes by effectively stimulating the biomechanical properties of the skin through the administration of a quite specific composition.

To the best knowledge of the inventors, the efficacy of these compounds, when they are administered by the oral or parenteral route for preventing and/or treating a deterioration of the biomechanical properties of the constituents of keratinous materials, more particularly of the dermis, has never been described.

Moreover, topical treatments for combating the cutaneous signs notably associated with aging are known. However, the topical active ingredients recommended do not always have an action at the level of the dermis, owing to poor penetration through the skin. Moreover, topical products act, by definition, locally on the zones to be treated, and they may be distributed nonuniformly on said zones, and require careful, repeated applications. They may in some cases cause cutaneous side effects, or discomfort.

In contrast, the oral route has the advantage of acting globally on all of the skin and in its deep layers (dermis, hypodermis), following a method of administration that is quick and not very restricting. In fact, the metabolites and other active nutrients are in particular distributed within the dermal matrix via the blood circulation. The oral route or administration by patch also offer the advantage of a method of administration that is quick and not very restricting.

The combination considered according to the invention even more particularly makes it possible to maintain and/or restore the properties of tonicity, firmness, pliability and/or density of the skin.

The invention relates in particular to the use of said combination for preventing and/or treating the cutaneous signs such as wrinkles and lines and/or for preventing and/or treating the cutaneous signs of fatigue such as periocular bags, periocular rings and skin that is dull and lacking radiance, preferably for preventing and/or treating periocular bags.

According to a preferred embodiment, the combination considered according to the invention makes it possible to prevent and/or treat the cutaneous signs of fatigue such as periocular bags, periocular rings and skin that is dull and lacking radiance.

It also makes it possible to improve the quality of the nails.

This combination proves quite particularly interesting in terms of beneficial effects on maintaining and/or restoring firmness of the skin in post-menopausal women. Thus, an increase in cellular activity of the dermis, an improvement of the quality of the extracellular matrix of the dermis and better hydration of the matrix gel of the extracellular matrix, have been demonstrated following oral administration of an oral supplement containing this combination.

The invention also relates to the use of a combination of lycopene, of vitamin C, of vitamin E and of at least one polyphenol compound derived from pine bark, as active ingredients for preparing a composition for oral and/or parenteral administration intended for promoting healing.

In particular, the compositions according to the invention are particularly useful for maintaining and/or restoring the properties of tonicity, firmness, pliability, and/or density of the skin.

It further relates to the cosmetic use by the oral route of a combination of lycopene, of vitamin C, of vitamin E and of at least one polyphenol compound derived from pine bark as active ingredients intended for improving the quality of the nails.

The invention also relates to a composition for oral and/or parenteral administration comprising, as single active principle, the combination of lycopene, of vitamin C, of vitamin E and of at least one polyphenol compound derived from pine bark.

It further relates to a composition for oral and/or parenteral administration comprising a combination of lycopene, of vitamin C, of vitamin E and of at least one polyphenol compound derived from pine bark, in which the value of the ratio of the content by weight of polyphenol compound to the sum of the contents by weight of lycopene, vitamin C and vitamin E is between 0.05 and 1.2, in particular between 0.2 and 1, and more particularly between 0.3 and 0.7.

Advantageously, said composition is moreover in the form of soft capsules, wrapped capsules, gels, dry or liquid emulsions, tablets, powders for dilution or oral ampules, or functional foods, for example yoghurts, drinks etc.

The compositions according to the invention are particularly useful for maintaining and/or restoring the properties of tonicity, firmness, pliability and/or density of the skin.

In particular, the combination of lycopene, of vitamin C, of vitamin E and of at least one polyphenol compound derived from pine bark is particularly useful for preparing a composition for oral and/or parenteral administration intended for preventing and/or treating the cutaneous signs associated with a deterioration of the aforementioned properties.

"Viscoelastic or biomechanical properties of the skin" means, within the scope of the present invention, the properties of extensibility, tonicity, firmness and/or pliability of the skin.

"Cutaneous signs" means any changes of the outward appearance of the skin, for example wrinkles, notably around the eyes and the corners of the lips, lines, withered skin, slack skin, flabby skin, thin skin, skin that is dull and lacking radiance, bags under the eyes, skin furrows, lack of skin elasticity and/or tone, but also all internal changes of the skin that are not always reflected in an altered outward appearance, for example all internal degradations of the skin, particularly of the collagen fibers, following exposure to ultraviolet radiation.

"Cutaneous signs of fatigue" means any changes of the outward appearance of the skin induced and/or accentuated by fatigue, a lack of sleep and/or a stressful life, for example periocular bags, periocular rings or skin that is dull and lacking radiance.

"Skin disorder induced by weight-reducing or slimming diets" means any changes of the outward appearance of the skin, for example the flabby skin appearance that may be more or less pronounced following weight loss.

"Skin disorder induced by cellulite" means any changes of the outward appearance of the skin, for example dimpling or "orange peel" which may be more or less localized in zones with excess weight such as the thighs, arms or abdomen.

It is understood within the scope of the present invention that "cosmetic use by the oral route" covers the use of products administered by the oral route, said products, for example in the form of dietary supplement or functional food as presented below for the case of the oral route, producing an effect on the skin with respect to aesthetic appearance and comfort, or for beauty, for example with a view to protecting it, maintaining it in good condition, modifying its appearance, and notably embellishing it.

Within the scope of the present invention, the parenteral route means intramuscular injection, intravenous injection or systemic administration by patch. In other words, this definition is intended to cover all methods of administration other than by the oral (or digestive) route in so far as the active ingredients are distributed by the blood circulation.

Systemic administration by patch is preferred as parenteral administration. Patches with exclusively local effect are excluded from the present invention.

"Transdermal device", "patch" or "system for transdermal delivery" means, in the sense of the invention, any system permitting active or passive release of the active substance by the transdermal route, i.e. permitting its transfer through the skin to the general systemic circulation.

Lycopene

The lycopene used according to the invention can be of natural or synthetic origin. Natural origin means lycopene, in the pure state or in solution regardless of its concentration in said solution, obtained from a natural component for example a vegetable extract, particularly tomato. Synthetic origin means lycopene, in the pure state or in solution regardless of its concentration in said solution, obtained by chemical synthesis.

When the lycopene is of natural origin, it can be obtained from vegetable material derived from a whole plant cultivated in vivo or derived from culture in vitro.

Cultivated in vivo means any culture of the conventional type, i.e. in soil in the open air or in a greenhouse, or without soil.

Culture in vitro means all techniques known by a person skilled in the art for obtaining a vegetable or a part of a vegetable artificially. The selection pressure imposed by the physicochemical conditions during growth of vegetable cells in vitro makes it possible to obtain a standardized vegetable material that is available throughout the year, in contrast to plants cultivated in vivo.

Preferably, according to the invention, a vegetable derived from culture in vivo is used. Very preferably according to the invention, a lycopene-rich tomato extract is used.

Lycopene is also present in melon, guava and grapefruit.

Any method of extraction known by a person skilled in the art can be used for preparing the lycopene used according to the invention.

The lycopene can be in aqueous suspension. For this, it is possible to use water-dispersible forms, cold or hot, such as those marketed by the company Lycored under the names Lyc-o-Mato CWD®.

As an example, according to the invention it is possible to use a lycopene-rich tomato extract, prepared by the company Lycored, marketed under the name LycOMato®, constituted of an oleoresin extract containing for example from 6 to 10% of pure lycopene.

Any other more complex lycopene-based ingredient can also be used for application of the invention.

Thus, more complex ingredient means for example a primary composition comprising lycopene and a whey protein. This primary composition is notably described in document WO 01/91588. This primary composition is also called lactolycopene. It is this ingredient that is used in the dietary supplement of example 1. It has the advantage of increasing the bioavailability of the lycopene and/or of being easily formulated in dietary supplements (as sachet, capsule, tablet, coated tablet, soft capsule, etc.)

The amount of extract usable according to the invention depends of course on the desired effect and can therefore vary widely.

To give an order of magnitude, it is possible to use lycopene in the pure state in an amount representing from 0.0001 to 50 wt. %, preferably from 0.001 to 10 wt. %, more preferably in an amount representing from 0.05 to 0.2 wt. % relative to the total weight of the composition.

For example, when the composition is more particularly intended for preventing and/or treating the cutaneous signs of fatigue such as periocular bags, periocular rings and skin that is dull and lacking radiance, it is possible to use lycopene in the pure state in an amount representing from 0.001 to 1 wt. %, notably from 0.005 to 0.1 wt. % relative to the total weight of the composition.

Of course, a person skilled in the art, if using the lycopene in the form of a solution, a vegetable extract for example, knows how to adjust the amount of solution that he uses in his composition so that the final amount of lycopene in the composition is in agreement with the amounts to be used, as defined above.

Vitamin C

According to the invention, vitamin C or ascorbic acid and/or its analogs can be used alone or in mixtures of any kind and in all proportions and can be of natural or synthetic origin.

The ascorbic acid is generally in the L form, as it is particularly in this form that it occurs in the vegetable kingdom.

The amount of vitamin C usable according to the invention depends of course on the desired effect and can therefore vary widely.

To give an order of magnitude, in the composition of the invention vitamin C in the pure state can be present at a content in the range from 0.0001 to 50 wt. %, preferably from 0.1 to 10 wt. %, and preferably at a content in the range from 3 to 6 wt. % relative to the total weight of the composition.

For example, when the composition is intended for preventing and/or treating the cutaneous signs of fatigue such as periocular bags, periocular rings and skin that is dull and lacking radiance, vitamin C in the pure state can be present at a content in the range from 0.001 to 5 wt. %, notably from 0.05 to 1 wt. % relative to the total weight of the composition.

Of course, if vitamin C is present in the form of a solution, for example a plant extract, a person skilled in the art will know how to adjust the amount of this solution in the composition according to the invention, so as to obtain the ranges of concentrations of vitamin C described above.

Vitamin E

Vitamin E can be present in the composition for oral and/or parenteral administration at a content in the range from 0.0001 to 50 wt. %, preferably from 0.1 to 10 wt. %, even more preferably from 0.5 to 2 wt. % relative to the total weight of the composition.

For example, when the composition is intended for preventing and/or treating the cutaneous signs of fatigue such as periocular bags, periocular rings and skin that is dull and lacking radiance, vitamin E can be present at a content in the range from 0.001 to 5 wt. %, notably from 0.005 to 1 wt. % relative to the total weight of the composition.

Polyphenol Compound

The polyphenol compounds comprise a large family of compounds that are very widely distributed in the vegetable kingdom. Thus, they are notably found in plants, from the roots to the fruits. Among the classes of polyphenols, we may notably mention flavonoids, proanthocyanidins, lignans, lignins, stilbenes, coumarins. Thus, the polyphenol compound used within the scope of the present invention can be in all of these forms mentioned above.

The polyphenol compounds can notably be derived from vegetable extracts selected from extracts of green tea, of grape such as *Vitis vinifera*, of pine and notably of pine bark, of apple, of bilberry, of hop, of guava, of cocoa, of wood such as chestnut, oak, horse-chestnut, hazel.

The term "polyphenol compound" within the scope of the present invention therefore also extends to the vegetable extract itself, rich in these polyphenol compounds.

The flavonoids represent the principal group of polyphenols.

The catechu polyphenols constitute, for their part, a subgroup of the flavonoids, which also comprise the flavanones, flavones and anthocyanins, and the flavonols.

The polyphenol compound is precisely a catechu polyphenol as defined below.

The subgroup of catechu polyphenols comprises a set of compounds isolated conventionally from plants such as cocoa, tea, grapevine and its derivatives, pine (*Pinus maritima*), cachou, certain fruits and having a variable degree of polymerization.

The base unit, also called catechin or catechol is pentahydroxy-3,5,7,3',4'dihydro-2,3-phenyl-2 chromene, which can be in the cis or trans form; epicatechin is its isomer, and can also be present in the cis or trans form.

The catechu polyphenols also include the various isomers of the base units (monomers), and oligomers (or proanthocyanidols) or polymers (tannins).

More particularly, the catechu polyphenols useful according to the invention are selected from the group comprising: catechin, epicatechin, gallocatechin, epigallocatechin and the salts, esters and/or derivatives thereof, in the form of monomers or oligomers.

When oligomers are used, they comprise advantageously from 2 to 14 base units, notably from 2 to 10.

Preferably their degree of polymerization is less than or equal to 5.

Compounds generally called proanthocyanidols or procyanidols, also called anthocyanin precursors or procyanidol oligomers (PCO), are used in particular. These oligomers will be degraded, partially, after absorption by the oral and/or parenteral route, releasing the monomers.

These polyphenols can be conjugated with sugars for example glucose, galactose, rhamnose, galacturonic acid.

"Catechu polyphenols" notably means, in the present text, mixtures of monomers and of the various oligomers having from 2 to 14 units, as defined previously, in all proportions.

Among the widely distributed dimers of the procyanidol family or procyanidol oligomers, use of which is particularly advantageous within the scope of the present invention, we may mention procyanidin B1, procyanidin B2, procyanidin B3 or procyanidin B6 or B7.

The procyanidins B1, B2, B3 are present in vegetable extracts of pine bark, of cocoa, of apple, of bilberry, of horse-chestnut, of hop, of guava and of hazel. Thus, the composition according to the present invention advantageously comprises one of these vegetable extracts.

The polyphenol compound present in the composition according to the present invention is derived from pine bark.

Said polyphenol compound derived from pine bark advantageously has a content of phenolic trimers that can range from 5 to 25 wt. %, preferably from 10 to 20 wt. % relative to the total weight of the polyphenol compound. Moreover, it advantageously has a content of polyphenolic dimers of at least 5 wt. % or that can range from 5 to 25 wt. %, preferably of at least 10 wt. % or that can range from 10 to 20 wt. % relative to the total weight of the polyphenol compound.

The polyphenol compound derived from pine bark also advantageously contains from 2 to 15 wt. %, for example from 5 to 10 wt. %, of phenolic acids such as ferulic acid, p-coumaric acid, caffeic acid and protocatechuic acid, relative to the total weight of the polyphenol compound.

Thus, the polyphenol compound, particularly advantageous for carrying out the invention, can have the following characteristics:

| Analysis/criterion | Specification |
| --- | --- |
| Drying loss | ≤5.0% |
| Sulfur ash | ≤0.4% |
| Insoluble in water (1% solution, T = 37° C.) | ≤5.0% |
| Insoluble in THF (1% solution, T = 20° C.) | ≤1.0% |
| pH (4% aqueous solution, T = 20° C.) | 2.5-4.5 |
| Polyphenolic trimers | 10-20% |
| Polyphenolic dimers | 10-20% |
| Taxifoliol + taxifoliol glucoside | >3% |
| Contents of phenolic acids [1] | 2-15% |

[1] ferulic + p-coumaric + protocatechuic + caffeic acids.

Also, according to one embodiment of the invention in its first and second aims, the polyphenol compound derived from pine bark is from an extract of maritime pine. Said extract of maritime pine is notably described in the article "A review of French Maritime Pine Bark Extract (PYCNOGENOL®), a herbal medication with a diverse clinical pharmacology", P. ROHDEWALD, International Journal of Clinical Pharmacology and Therapeutics, Vol. 40-No 4/2002(158-168).

The composition according to the invention preferably comprises the polyphenol compound at a content in the range from 0.0001 to 50 wt. % and preferably from 0.001 to 10 wt. %, even more preferably from 0.5 to 2 wt. % relative to the total weight of the composition.

For example, when the composition is intended for preventing and/or treating the cutaneous signs of fatigue such as periocular bags, periocular rings and skin that is dull and lacking radiance, the polyphenol compound can be present at a content in the range from 0.001 to 5 wt. %, notably from 0.1 to 1 wt. % relative to the total weight of the composition.

As shown in the examples given below, the inventors have demonstrated that a composition containing lycopene, vitamin C, vitamin E and a polyphenol compound derived from pine bark in the required ratio of contents could act favorably on the dermal matrix, by increasing the cellular activity of the dermis, improving the quality of the extracellular matrix of the dermis and by better hydration of the matrix gel of the extracellular matrix.

A composition according to the present invention is thus intended for combating the cutaneous signs of aging and quite particularly is intended for maintaining and/or restoring the biomechanical properties of the skin.

Thus, as already stated, the composition according to the invention is particularly useful for maintaining and/or restoring the properties of tonicity, firmness, pliability and/or density of the skin.

Consequently, the composition according to the invention is intended in particular for the prevention and/or cosmetic treatment of skin disorders induced by chronological aging, in particular of mature skin of pre- or post-menopausal women, but also for the prevention and/or cosmetic treatment of disorders induced by photoaging.

The composition according to the invention is therefore also suitable for the prevention and/or treatment of skin disorders induced by the menopause.

Thus, the present invention relates, according to one of its preferred embodiments, to the cosmetic use of a composition according to the present invention as a composition intended for the prevention and/or treatment of skin disorders induced by the menopause.

The composition according to the invention is also particularly suitable for the prevention and/or cosmetic treatment of skin disorders induced by weight loss such as is observed during slimming and/or weight-reduction diets, such as sagging of supporting tissues, loss of skin tonicity and pliability, and increased visibility of dimpling.

The invention also relates to the cosmetic use of a composition according to the present invention as a composition intended for combating lack of skin pliability and/or tone.

The invention finally relates to the cosmetic use of a composition according to the invention as a composition intended for preventing and/or treating the visual appearance associated with cellulite, such as dimpling and "orange peel".

As illustrated in example 1, the gene of the vitamin is significantly increased, so that it appears that the combination according to the present invention has a favorable action on healing.

The invention also relates to the cosmetic use of a composition according to the present invention as a composition intended for preventing and/or treating cutaneous signs such as wrinkles and lines and/or for preventing and/or treating the cutaneous signs of fatigue such as periocular bags, periocular rings and skin that is dull and lacking radiance.

The invention extends to the cosmetic use by the oral and/or parenteral route of a composition according to the invention as a composition intended for promoting healing.

According to a preferred embodiment, lycopene is present in this composition at a content in the range from 0.05 to 0.2 wt. %, vitamin C is present at a content in the range from 3 to 6 wt. %, vitamin E is present at a content in the range from 0.5 to 2 wt. %, and the polyphenol compound is present at a content in the range from 0.5 to 2 wt. %, relative to the total weight of the composition.

When the composition is more particularly intended for preventing and/or treating the cutaneous signs of fatigue such as periocular bags, periocular rings and skin that is dull and lacking radiance, lycopene is present in this composition at a content in the range from 0.005 to 0.1 wt. %, vitamin C is present at a content in the range from 0.05 to 1 wt. %, vitamin E is present at a content in the range from 0.005 to 1 wt. %, and the polyphenol compound is present at a content in the range from 0.1 to 1 wt. %, relative to the total weight of the composition.

According to yet another preferred embodiment, the value of the ratio of the content by weight of polyphenol compound to the sum of the contents by weight of lycopene, vitamin C and vitamin E is between 0.2 and 1 and even more preferably between 0.3 and 0.7.

When the composition is more particularly intended for preventing and/or treating the cutaneous signs of fatigue such as periocular bags, periocular rings and skin that is dull and lacking radiance, the value of the ratio of the content by weight of polyphenol compound to the sum of the contents by weight of lycopene, vitamin C and vitamin E is between 0.3 and 0.7 and even more preferably between 0.4 and 0.6.

Additional Active Ingredients

According to an advantageous embodiment of the invention, the claimed use can employ the combination according to the invention with in addition at least one nutritional antiaging active ingredient, a photoprotective nutritional active ingredient, a nutritional active ingredient for the menopause and/or a nutritional active ingredient for slimming.

Among the antiaging nutritional active ingredients, we may notably mention dietary antioxidants, nutrients with antiradical properties and cofactors of endogenous antioxidant enzymes: vitamin A, carotenoid, xanthophylls, isoflavones, certain minerals such as zinc, copper, magnesium, selenium, lipoic acid, co-enzyme Q10, superoxide dismutase (SOD), or taurine. Among antiaging active ingredients, we may notably mention the nonsaponifiable fractions extracted from lipids of vegetable origin, aloe vera, native or hydrolyzed marine collagen, vegetable or marine oils rich in omega-3 fatty acids, in omega-6 (including gamma-linolenic acid), etc.

Among the photoprotective nutritional active ingredients, we may notably mention: antioxidants and antiradical agents: vitamin A, carotenoids, xanthophylls, certain minerals such as zinc, copper, magnesium, selenium, co-enzyme Q10, superoxide dismutase (SOD), probiotics.

We may also mention the nutritional ingredients displaying hydrating properties or immunomodulating properties: probiotics, extract of Polypodium leucotomos, vegetable or marine oils rich in ω-3 fatty acids, in ω-6, including gamma-linolenic acid.

Among the nutritional active ingredients that are active on the clinical signs of the menopause (for example hot flushes, etc.), we may notably mention isoflavones, lignans, DHEA, extracts of yam, of sage, of hop, calcium, magnesium, hydrolyzates of proteins, vegetable or marine oils rich in omega-3 fatty acids, etc.

Of course, polyphenol compounds other than the polyphenol compound derived from pine bark, notably as described above, can additionally be incorporated in the composition according to the present invention.

Among the nutritional ingredients employed in the area of slimming, we may notably mention: green tea, mate, horsechestnut, cola, caffeine, theobromine, synephrine, bromelain, ephedra, citrus aurantium, calcium, hoodia, garcinia, chitosan, vegetable fibers (cactus, apples, pineapple, etc.), fennel, blackcurrant, meadowsweet, black radish, etc.

Composition

A combination according to the invention is administered by the oral and/or parenteral route. The corresponding compositions can be in all the pharmaceutical forms normally used according to the method of administration in question.

In the case of the oral route, it can be a composition of the dietary supplement type or a functional food, or else a pharmaceutical composition.

A composition according to the invention can notably be in the form of soft capsules, wrapped capsules, gels, dry or liquid emulsions, tablets, powders for dilution or oral ampules or any other form known by a person skilled in the art. The composition can optionally contain suitable excipients such as colorants, sweeteners, flavorings, fillers, binders, preservatives, etc.

According to another preferred embodiment of the invention, lycopene, vitamin C, vitamin E and the polyphenol compound can also be incorporated in dietary matrices for producing functional foods such as food bars, enriched foods such as oils, butters, margarines, compacted powders, fibers or in the form of emulsion in drinks.

Thus, the composition according to the invention can be a functional food.

The composition can moreover contain other antioxidants, other vitamins, minerals permitted in Europe in dietary supplements as described in directive EC 2002/46.

In the case of administration by the parenteral route, a composition can be in the form of an injectable solution or a patch or system for transdermal delivery.

As a guide, the doses of lycopene supplied for achieving the aims of the invention will be adapted in relation to the desired effect. For example, a dose in the range from 1 to 22 mg can be envisaged, for example in the range from 2 to 11 mg/day, or even from 4 to 7 mg/day.

Moreover, the doses of polyphenol compounds in the form of monomer or of oligomer supplied for achieving the aims of the invention can vary from 6 to 75 mg, for example from 13 to 75 mg, notably from 20 to 75 mg/day, and more particularly from 30 to 50 mg/day.

Moreover, the doses of vitamin C supplied for achieving the aims of the invention can vary from 10 to 105 mg, for example from 20 to 105 mg, notably from 33 to 105 mg/day, advantageously from 50 to 70 mg/day.

Finally, the doses of vitamin E supplied for achieving the aims of the invention can vary from 1 to 17 mg, for example from 3 to 17 mg, notably from 6 to 17 mg/day, advantageously from 9 to 11 mg/day.

When the combination according to the invention is more particularly intended for preventing and/or treating the cutaneous signs of fatigue such as periocular bags, periocular rings and skin that is dull and lacking radiance, preferably for preventing and/or treating periocular bags, the daily dose of lycopene can be between 2 and 11 mg and/or the daily dose of vitamin C can be between 20 and 70 mg and/or the daily dose of vitamin E can be between 3 and 12 mg and/or the daily dose of polyphenol compound can be between 13 and 50 mg.

According to one embodiment, the invention relates to a composition for oral administration comprising a combination of lycopene, of vitamin C, of vitamin E and of at least one polyphenol compound derived from pine bark, in which the value of the ratio of the content by weight of polyphenol compound to the sum of the contents by weight of lycopene, vitamin C and vitamin E is between 0.3 and 0.7, characterized in that it is in the form of soft capsules, wrapped capsules, gels, dry or liquid emulsions, tablets, powders for dilution or oral ampules, or functional foods, for example yoghurts, drinks, etc.

The invention also relates to the use of a combination according to the invention for preparing a composition for oral and/or parenteral administration intended for preventing and/or treating the cutaneous signs of aging and/or of fatigue, preferably the cutaneous signs of fatigue, and notably periocular bags.

In particular, the combination of lycopene, of vitamin C, of vitamin E and of at least one polyphenol compound derived from pine bark is particularly useful for preparing a composition for oral and/or parenteral administration intended for preventing and/or treating the cutaneous signs of aging associated with loss of extensibility, of tonicity, of firmness, of pliability, of density and/or of elasticity of the skin.

The compositions according to the invention can be cosmetic, dermatological or pharmaceutical compositions.

In the sense of the present invention, a cosmetic composition denotes a composition for producing an effect on the skin with respect to aesthetic appearance and comfort, or for beauty, for example with a view to protecting it, maintaining it in good condition, altering its appearance, and notably embellishing it. It can be in the form of a nutritional product.

The present invention is illustrated by the examples which follow.

EXAMPLE 1

Exploratory Clinical Study Relating to Quantification of the Reference mRNAs Induced by Taking Dietary Supplement A Formula of Dietary Supplement A Pharmaceutical form: film-coated tablets Posology: 2 tablets/day Formula Dietary Supplement A

TABLE 1

| | Common name of ingredient/excipient | Composition (mg/cp) |
|---|---|---|
| NUTRITIONAL INGREDIENTS | Lactolycopene 2% [1] | 100.00 |
| | Vitamin C (90%) [2] | 28.9 |
| | Extract of maritime pine bark [3] | 13.3 |
| | Vitamin E [4] | 4.9 |

[1] 2% of lycopene.
[2] 90% of L-ascorbic acid
[3] Complying with the specifications of the monograph USP28, Maritime Pine Extract, Appendix A (a). Of which: 65 to 75% of procynanidins; ≤8% loss on drying.
[4] Complying with the specifications of the USP monograph (Vitamin E), Ph. Eur. 5 (RRR-alpha-Tocopheryl Hydrogen Succinate) and FCC IV (d-alpha-Tocopheryl Acid Succinate).

Dietary supplement A is preferably intended for post-menopausal women who have loss of firmness of the skin.

Objective of the Clinical Test

To evaluate the effect of dietary supplement A versus placebo, on cutaneous biomarkers that may be associated with a change in biomechanical properties of the skin after 2 months of taking dietary supplement A.

Methodology

Study lasting 2 months on 18 women post-menopausal for more than two years (9 in the group taking dietary supplement A/9 in the placebo group), aged over 50 years, not receiving hormone replacement therapy, and with lack of firmness of the skin on the inner surface of the arm.

Biopsies of 3 mm performed on the arm at T0 and T2 months for extraction of total mRNAs.

Quantification of specific mRNAs coding for proteins that may be associated with a change in biomechanical properties of the skin.

Preparation of the mRNAs for RT-PCR

The two biopsies were pooled, ground in liquid nitrogen (Mikro Dismenbrator S, B. Braun Biotech International), then the total RNA was extracted and purified by ultracentrifugation on cesium chloride gradient. The amount of RNA purified was evaluated by measuring the OD (optical density) at 260 nm (Nanodrop) and the quality of the RNA extracted was validated by calculating the OD260/OD280 ratio. The integrity of the RNAs extracted was also verified using the BioAnalyzer from Agilent. Stock solutions of RNA were prepared in order to obtain a concentration close to 1.25 ng/µl.

Evaluation of the Amount of Cutaneous Biomarkers

The concentration of RNA was normalized relative to the amount of ribosomal RNA 28S. The technique of RT-PCR was made quantitative by adding, in each reaction tube, an internal standard of known concentration, made up of a synthetic RNA, which will be co-transcribed and co-amplified at the same time as the required RNA. The samples corresponding to T0 and T2 from each volunteer were analyzed in the same series, and underwent deposition and migration on the same polyacrylamide gel. Statistical analysis was performed using a unilateral paired-sample Student test, comparing the values at T0 and at T2 in each group. A ratio T2/T0=1.00 signifies that the two values are comparable. A ratio T2/T0 >1.00 reflects an increase of the transcript investigated. Conversely, a ratio T2/T0 <1.00 reflects a decrease in expression of the mRNA investigated.

Results/Quantification of Target mRNAs

TABLE II expression of target biomarkers after taking dietary supplement A (versus placebo)

| | PLACEBO (n = 9) | T2/T0 t test paired | DIETARY SUPPLEMENT A (n = 9) | t test paired |
|---|---|---|---|---|
| VIM | 1.02 ± 0.36 | NS | 1.24 ± 0.25 | 0.03 |
| DEC | 1.33 ± 0.58 | NS | 1.40 ± 0.51 | 0.03 |
| FIBMOD | 1.17 ± 0.44 | NS | 1.48 ± 0.57 | 0.02 |
| LUM | 1.25 ± 0.53 | NS | 1.40 ± 0.30 | 0.002 |
| XYL | 0.92 ± 0.27 | NS | 1.25 ± 0.27 | 0.01 |

VIM: vimentin; DEC: decorin; LUM: lumican; FIBMOD: fibromodulin; XYL: xylosyltransferase.

In the group who took the dietary supplement, the mRNA coding for vimentin is significantly increased (p=0.03). In cells of mesenchymal origin, such as fibroblasts and endothelial cells, vimentin is a major structural component of the intermediate filaments. This network of the cytoskeleton is directly involved in cellular mechanical functions. In particular, low expression of vimentin affects the healing processes. Cells deficient in vimentin notably have low mechanical stability as well as reduced motility and contractile properties. Moreover, vimentin participates in the three-dimensional organization of focal complexes, organization of actin-dependent microfilaments and interactions with the extracellular matrix. Certain of these interactions are directly affected by skin aging such as those that have an influence on control of cellular migration, proliferation and contraction or on control of the metabolic phenotype.

Investigation of the mRNA of vimentin therefore indicates that dietary supplement A has a favorable action on the cytoskeleton of the fibroblasts. This is a sign of increased activity of the cell.

Moreover, the mRNA coding for decorin is overexpressed significantly after taking dietary supplement A (p=0.03), whereas expression of this mRNA is not altered after taking placebo. Decorin is a small glycosylated protein (proteoglycan) which belongs to the family of Small Leucine-Rich Proteoglycans (SLRP). Decorin is present in the whole of the dermis, but is not present in the epidermis. It is synthesized and secreted by the fibroblasts. Its main role is regulation of collagen fibrillogenesis. In fact, decorin contributes to good cohesion of collagen fibers: by fixing to the fibers, it allows them to organize and form a collagen bundle. It has been shown that decorin decreases with age.

The results for decorin show that dietary supplement A seems to have a stabilizing effect on the structure of collagen fibers and therefore contributes to improvement of the quality of the extracellular matrix of the dermis.

After taking the supplement, we also recognized a significant increase in mRNAs coding for other Small Leucine-Rich Proteoglycans (SLRP), in particular those of lumican (p=0.002) and of fibromodulin (p=0.02) which are strongly involved in fibrillogenesis and hydration of the perifibrillar spaces.

Finally, another mRNA was overexpressed significantly after taking dietary supplement A. This is the mRNA coding for xylosyltransferase (p=0.01), which is the first enzyme involved in the synthesis of proteoglycans of the chondroitin sulfate or dermatan sulfate type in fibroblasts. Xylosyltransferase is the enzyme that initiates glycosylation, i.e. fixation of sugars on the central protein chain of proteoglycan. The proteoglycans then go into the extracellular matrix where they form a hydrated gel by absorbing water molecules. The skin cells as well as collagen and elastin fibers are bathed in this gel. The proteoglycans play a role not only as aqueous reservoir so that forces of compression can be resisted, but also an organizational role in the structure of the matrix and in transmission of information. The proteoglycans decrease with age which leads to a degradation of the matrix gel. By acting on xylosyltransferase, dietary supplement A participates in part in restoring the quality of this gel. By providing better fixation of water molecules, this hydrated matrix gel makes it possible to "re-swell" the dermis and therefore improve the surface condition of the skin.

Conclusions

Taken together, these results show that dietary supplement "A" has a global action on the quality of the dermis:

1) by increasing the metabolism of the fibroblasts, through increased transcription of the gene of vimentin, a key protein of the cytoskeleton;

2) by improving the hydrated gel of the extracellular matrix in which the fibers and cells of the dermis are bathed, through increased transcription of the gene of xylosyltransferase, the first enzyme involved in the formation of proteoglycans;

3) by structuring the collagen fibers, through increased transcription of the gene of lumican, fibromodulin and decorin, proteoglycans involved in fibrillogenesis.

EXAMPLE 2

Evaluation of the Efficacy of Dietary Supplement A Versus Placebo on the Biomechanical Properties of the Skin The formula of the dietary supplement and its administration posology are as employed in example 1.

Objective of the clinical test: Investigation of the effect of taking dietary supplement A on the deterioration of the biomechanical properties of the skin and of the microrelief of the skin.

Methodology

Single-center, double blind study on 2 groups, one of which is a placebo group. A procedure of randomization with constraints was performed to ensure better comparability of the groups at inclusion.

Seventy-two healthy female volunteers, aged from 40 to 65 years and meeting the criteria for inclusion and noninclusion participated in this study, with a total duration of 6 months.

Dietary supplement A: n=49.

Placebo: n=23

The efficacy of dietary supplement A was evaluated:

by a dermatologist by means of various photographic atlases by a dermatologist according to a 6-point clinical score from 0 to 5. The more the state of the parameter is regarded as good, the closer the score is to 5 and vice versa.

by instrumental measurements (Torquemeter® and image analysis based on skin prints).

by a self-assessment questionnaire completed by the volunteers.

Measurement with the Torquemeter®

The Torquemeter® is a noninvasive device. The measuring head of the DTM is composed of a moving central disk 20 mm in diameter and of a fixed circular plate. This device is affixed on the skin by means of fixed, concentric double-sided adhesive tape. The angle of rotation of the central disk is measured by an angular sensor of very high resolution. During application of the measuring head, the central disk swivels. A torsional stress with an angle Ue is then applied to the zone of the skin between the moving central disk and the peripheral fixed ring (rapid deformation). Then the angle of rotation continues to increase at a reduced rate with an angle Uv.

After stopping the torsional moment, skin returns to its initial state in two stages, rapid (deformation Ur) and slow as far as the origin.

The precise measurement zones are marked by means of a mask of circular shape. The parameters measured are (Ue, Uv, Ur).

Analysis of Images from Skin Prints

A negative replica of the wrinkles of the surface of the skin is prepared using silicone rubber. For analysis, this print is illuminated by grazing light, which generates shadows behind each wrinkle.

Analysis of the wrinkles is performed using Toposurf software.

Results

Dermatologic Evaluation by Means Photographic Atlases

TABLE 2

| | | | | | | |
|---|---|---|---|---|---|---|
| | | | Variation of cutaneous signs - Dietary supplement A | | | |
| PARAMETERS | T0 (mean ± SD) | T12 (mean ± SD) | T12/T0 Tukey test for multiple comparisons | T24 (mean ± SD) | T24/T0 Tukey test for multiple comparisons | Analysis of variance |
| Depth of crow's-feet wrinkles | 3.3 ± 1.1 | 2.6 ± 0.9 | IMPROVEMENT $p = 0.003$ | 2.8 ± 1.0 | IMPROVEMENT $p = 0.045$ | IMPROVEMENT $p = 0.004$ |
| Bags | 2.4 ± 1.2 | 2.0 ± 1.4 | NS | 1.8 ± 1.2 | IMPROVEMENT $p = 0.034$ | IMPROVEMENT $p = 0.042$ |
| Wrinkles at corner of lips | 2.7 ± 1.7 | 1.9 ± 1.7 | IMPROVEMENT $p = 0.048$ | 1.9 ± 1.7 | NS (trend, $p = 0.055$) | IMPROVEMENT $p = 0.027$ |

SD: standard deviation

TABLE 3

| | | | | | | |
|---|---|---|---|---|---|---|
| | | | Variation of cutaneous signs - Placebo | | | |
| PARAMETERS | T0 (mean ± SD) | T12 (mean ± SD) | T12/T0 Tukey test for multiple comparisons | T24 (mean ± SD) | T24/T0 Tukey test for multiple comparisons | Analysis of variance |
| Depth of crow's-feet wrinkles | 3.3 ± 1.3 | 2.8 ± 1.2 | NS | 2.7 ± 1.1 | NS | NS |
| Bags | 1.9 ± 1.1 | 1.9 ± 1.2 | NS | 2.0 ± 1.3 | NS | NS |
| Wrinkles at corner of lips | 2.5 ± 1.5 | 1.6 ± 1.5 | NS | 2.2 ± 1.8 | NS | NS |

SD: standard deviation;
NS: not statistically significant

In the group who had taken dietary supplement A, the depth of crow's-feet wrinkles is statistically reduced starting from 12 weeks. Taking dietary supplement A also leads to a statistically significant decrease in wrinkles at the corner of the lips starting from 12 weeks, as well as of bags under the eyes at 24 weeks. These parameters show no change in the placebo group.

Dermatologic evaluation according to the clinical score

TABLE 4

Variation of cutaneous signs - Dietary supplement A

| PARAMETERS | T0 (mean ± SD) | T12 (mean ± SD) | T12/T0 Tukey test for multiple comparisons | T24 (mean ± SD) | T24/T0 Tukey test for multiple comparisons | Analysis of variance |
|---|---|---|---|---|---|---|
| Pliability of the skin | 2.7 ± 0.9 | 3.4 ± 0.8 | IMPROVEMENT p = 3.32E−04 | 3.6 ± 0.8 | IMPROVEMENT p = 3.36E−04 | IMPROVEMENT p = 2.19E−06 |
| Lines | 2.5 ± 1.0 | 2.9 ± 1.0 | NS | 3.3 ± 1.0 | IMPROVEMENT p = 0.001 | IMPROVEMENT p = 0.001 |
| Wrinkles on the face | 2.3 ± 1.0 | 2.9 ± 1.0 | IMPROVEMENT p = 0.01 | 2.8 ± 0.9 | IMPROVEMENT p = 0.032 | IMPROVEMENT p = 0.007 |
| Wrinkles on cleavage | 3.2 ± 1.4 | 3.2 ± 1.0 | NS | 4.1 ± 1.1 | IMPROVEMENT p = 0.001 | IMPROVEMENT p = 1.83E−04 |

SD: standard deviation;
NS: not statistically significant

TABLE 5

Variation of cutaneous signs - Placebo

| PARAMETERS | T0 (mean ± SD) | T12 (mean ± SD) | T12/T0 Tukey test for multiple comparisons | T24 (mean ± SD) | T24/T0 Tukey test for multiple comparisons | Analysis of variance |
|---|---|---|---|---|---|---|
| Pliability of the skin | 2.7 ± 0.9 | 3.2 ± 0.8 | NS | 3.2 ± 0.9 | NS | NS |
| Lines | 2.9 ± 1.1 | 3.2 ± 1.0 | NS | 3.5 ± 0.9 | NS | NS |
| Wrinkles on the face | 3.0 ± 1.1 | 3.2 ± 1.1 | NS | 3.3 ± 1.3 | NS | NS |
| Wrinkles on cleavage | 4.0 ± 0.7 | 3.3 ± 1.1 | DETERIORATION p = 0.047 | 4.5 ± 1.1 | NS | p = 0.001 |

SD: standard deviation;
NS: not statistically significant

Dietary supplement A produces a statistically significant improvement of the cutaneous signs, namely wrinkles and lines, as well as of the pliability of the skin. The placebo does not alter these parameters.

Instrumental Evaluation

Measurement with Torquemeter® after 6 Months of Supplementation with Dietary Supplement A or Placebo.

TABLE 6

Variation of the biomechanical properties of the skin- Dietary supplement A

| PARAMETERS | T0 (mean ± SD) | T24 (mean ± SD)) | T24/T0 Analysis of variance |
|---|---|---|---|
| Ue (extensibility) | 2.91 ± 0.571 | 3.207 ± 0.687 | IMPROVEMENT $p = 0.023$ |
| Uv (plasticity) | 1.894 ± 0.438 | 2.085 ± 0.376 | IMPROVEMENT $p = 0.024$ |
| Ur (tonicity) | 1.099 ± 0.175 | 1.253 ± 0.240 | IMPROVEMENT $p = 0.001$ |

SD: standard deviation

TABLE 7

Variation of the biomechanical properties of the skin- Placebo

| PARAMETERS | T0 (mean ± SD) | T24 (mean ± SD) | T24/T0 Analysis of variance |
|---|---|---|---|
| Ue (extensibility) | 3.189 ± 0.695 | 3.179 ± 0.645 | NS |
| Uv (plasticity) | 1.960 ± 0.389 | 2.092 ± 0.340 | NS |
| Ur (tonicity) | 1.131 ± 0.167 | 1.209 ± 0.168 | NS |

SD: standard deviation; NS: not statistically significant

After taking dietary supplement A for 6 months, the parameters relating to the biomechanical properties of the skin are statistically improved. These parameters are not altered by taking the placebo.

Analysis of Images from Skin Prints after 6 Months of Supplementation with Dietary Supplement A or Placebo.

TABLE 8

Variation of skin topography- Dietary supplement A

| PARAMETERS | T0 (mean ± SD) | T24 (mean ± SD) | T24/T0 Analysis of variance |
|---|---|---|---|
| SRvm (mean height of valleys) | 0.059 ± 0.009 | 0.053 ± 0.01 | IMPROVEMENT $p = 0.026$ |
| Density < Z1 (density of furrows with a height ≤ 10 μm) | 8.06 ± 7.187 | 14.402 ± 10.192 | IMPROVEMENT $p = 0.019$ |
| Density > Z2 (density of furrows with a height > 20 μm) | 73.307 ± 14.935 | 55.733 ± 18.878 | IMPROVEMENT $p = 0.001$ |
| Anisotropy (density of furrows as a function of their height and their orientation) | 43.926 ± 14.561 | 34.011 ± 12.114 | IMPROVEMENT $p = 0.016$ |

TABLE 9

Variation of skin topography - Placebo

| PARAMETERS | T0 (mean ± SD) | T24 (mean ± SD) | T24/T0 Analysis of variance |
|---|---|---|---|
| SRvm (mean height of valleys) | 0.059 ± 0.019 | 0.053 ± 0.01 | NS |
| Density < Z1 (density of furrows with a height ≤10 μm) | 13.763 ± 12.956 | 16.76 ± 8.729 | NS |
| Density > Z2 (density of furrows with a height > 20 μm) | 65.231 ± 22.12 | 52.168 ± 18.494 | NS |
| Anisotropy (density of furrows as a function of their height and their orientation) | 39.117 ± 16.255 | 33.224 ± 13.099 | NS |

SD: standard deviation;
NS: not statistically significant

The relief of the skin is very fine and is only visible by means of a dermatological magnifying glass in children, whereas it becomes visible to the naked eye in old age. Moreover, the relief of the skin is correlated with the mechanical properties of the dermis. The collagen fibers of the deep dermis, which are interlaced, keep the skin taut in young people by forming a compact network. This network becomes disorganized with age, the skin sags, and the furrows become deeper. The skin topography reveals a particular network: parallel and criss-cross furrows forming rectangles, squares, trapeziums, diamonds and triangles. The primary lines are wide and from 20 to 100 μm deep depending on site and age. The secondary lines are narrow.

Taking dietary supplement A for 6 weeks leads to a statistically significant improvement in skin anisotropy, an increase in the density of secondary furrows (Density<Z1) and a decrease in primary furrows (Density>Z2). These parameters are unchanged in the placebo group. In other words, dietary supplement A leads to a reappearance of secondary furrows (Density<Z1), which are characteristic of young skin, a decrease in the depth of primary furrows (Density>Z2), which are characteristic of aged skin, and a decrease in skin anisotropy, which normally increases with age.

Self-Assessment by the Volunteers

The quality of the nails was assessed by the volunteers using a visual analog scale (0 cm: poor quality; 10 cm: good quality). An increase in the measurement is therefore synonymous with improvement.

TABLE 10

Variation of quality of the nails - Dietary supplement A

| PARAMETER | T0 (mean ± SD) | T6 (mean ± SD) | T6/T0 Tukey test for multiple comparisons | T12 (mean ± SD) | T12/T0 Tukey test for multiple comparisons | T24 (mean ± SD) | T24/T0 Tukey test for multiple comparisons |
|---|---|---|---|---|---|---|---|
| Quality of the nails | 4.24 ± 2.96 | 6.13 ± 2.11 | IMPROVEMENT p = 4.68E−04 | 6.48 ± 2.16 | IMPROVEMENT p = 2.19E−05 | 6.48 ± 1.93 | IMPROVEMENT p = 2.11E−05 |

SD: standard deviation

TABLE 11

Variation of quality of the nails - Placebo

| PARAMETER | T0 (mean ± SD) | T6 (mean ± SD) | T6/T0 Tukey test for multiple comparisons | T12 (mean ± SD) | T12/T0 Tukey test for multiple comparisons | T24 (mean ± SD) | T24/T0 Tukey test for multiple comparisons |
|---|---|---|---|---|---|---|---|
| Quality of the nails | 4.85 ± 2.90 | 5.83 ± 2.26 | NS | 6.47 ± 2.23 | NS | 6.52 ± 2.35 | NS |

SD: standard deviation;
NS: not statistically significant

The quality of the nails is improved statistically significantly in the volunteers taking dietary supplement A. Taking the placebo does not alter this parameter.

Conclusions

Taken together, these results show that dietary supplement A makes it possible to correct the undesirable signs, notably cutaneous, associated with loss of biomechanical characteristics in particular of the skin, improving the topography as well as the relief of the skin. Dietary supplement A aids in restructuring the skin on the inside for a skin that is firmer and for tangible results at the surface.

The invention claimed is:

1. A method for treating bags and rings under the eyes comprising orally administering a composition comprising lycopene, vitamin C, vitamin E, and at least one polyphenol compound derived from pine bark as active ingredients.

2. The method as claimed in claim 1, wherein a value of the ratio of the content by weight of the polyphenol compound to a sum of the contents by weight of the lycopene, the vitamin C, and the vitamin E is between 0.05 and 1.2.

3. The method as claimed in claim 1, wherein a daily dose of the lycopene is between 1 and 22 mg.

4. The method as claimed in claim 1, wherein a daily dose of the vitamin C is between 10 and 105 mg.

5. The method as claimed in claim 1, wherein a daily dose of the vitamin E is between 1 and 17 mg.

6. The method as claimed in claim 1, wherein a daily dose of the polyphenol compound is between 6 and 75 mg.

7. The method as claimed in claim 1, wherein the composition maintains and/or restores the properties of tonicity, firmness, pliability, and/or density of the skin.

8. The method as claimed in claim 1, wherein the composition improves the quality of the nails.

9. The method as claimed in claim 1, wherein the composition combats cutaneous signs induced by weight loss.

10. The method as claimed in claim 1, wherein the composition prevents and/or treats skin disorders induced by menopause.

11. The method as claimed in claim 1, wherein the composition combats lack of skin elasticity and/or tone.

12. The method as claimed in claim 1, wherein the composition prevents and/or treats the visual appearance associated with cellulite.

13. The method as claimed in claim 1, wherein the composition treats cutaneous signs of fatigue, periocular bags, periocular rings, and skin that is dull and lacking radiance.

14. The method as claimed in claim 13, wherein the composition treats periocular bags and a daily dose of the lycopene is between 2 and 11 mg, and/or a daily dose of the vitamin C is between 20 and 70 mg, and/or a daily dose of the vitamin E is between 3 and 12 mg, and/or a daily dose of the polyphenol compound is between 13 and 50 mg.

15. The method as claimed in claim 1, wherein the polyphenol compound derived from pine bark has a content of phenolic trimers that range from 5 to 25 wt.% relative to the total weight of the composition.

16. The method as claimed in claim 1, wherein the polyphenol compound derived from pine bark has a content of polyphenolic dimers of at least 5 wt.% relative to the total weight of the composition.

17. The method as claimed in claim 1, wherein the polyphenol compound derived from pine bark has a content of phenolic acids from 2 to 15 wt.% relative to the total weight of the composition.

18. The method as claimed in claim 1, wherein the lycopene is lactolycopene.

* * * * *